United States Patent [19]

Shapiro

[11] Patent Number: 4,472,393
[45] Date of Patent: Sep. 18, 1984

[54] 3,20-DIOXO-1,4-PREGNADIENE-17α-OL 17-AROMATIC HETEROCYCLE CARBOXYLATES

[75] Inventor: Elliot L. Shapiro, Cedar Grove, N.J.

[73] Assignee: Schering Corporation, Kenilworth, N.J.

[21] Appl. No.: 403,276

[22] Filed: Jul. 29, 1982

Related U.S. Application Data

[63] Continuation-in-part of Ser. No. 230,763, Feb. 2, 1981, abandoned.

[30] Foreign Application Priority Data

Jan. 25, 1982 [EP] European Pat. Off. ............ 82100490

[51] Int. Cl.$^3$ ............................................. A61K 31/56
[52] U.S. Cl. ................................ 424/243; 260/397.45
[58] Field of Search .................... 260/397.45; 424/243

[56] References Cited

U.S. PATENT DOCUMENTS

| 3,422,193 | 1/1969 | Shapiro et al. | 260/397.45 |
| 3,557,158 | 1/1971 | Lincoln et al. | 260/397.45 |
| 3,721,687 | 3/1973 | Elks et al. | 260/397.45 |
| 3,784,692 | 1/1974 | Ercoli et al. | 424/243 |
| 3,980,778 | 9/1976 | Ager et al. | 424/243 |
| 4,226,862 | 10/1980 | Riva et al. | 424/243 |
| 4,275,061 | 6/1981 | Riva et al. | 260/397.45 |

OTHER PUBLICATIONS

Oliveto et al., "Journal Amer. Chem. Soc." vol. 42, (1958), p. 4431.
C.A., vol. 59, (1963), Par. 14,077.

Primary Examiner—Elbert L. Roberts
Attorney, Agent, or Firm—Anita W. Magatti; Gerald S. Rosen

[57] ABSTRACT

This invention relates to novel 3,20-dioxo-1,4-pregnadiene-17α-ol 17-aromatic heterocyclic carboxylates, to pharmaceutical formulations thereof, and their use in the treatment and control of inflammatory conditions.

31 Claims, No Drawings

3,20-DIOXO-1,4-PREGNADIENE-17α-OL 17-AROMATIC HETEROCYCLE CARBOXYLATES

FIELD OF INVENTION

This application is a continuation-in-part of Ser. No. 230,763, filed Feb. 2, 1981, now abandoned.

This invention relates to novel 3,20-dioxo-1,4-pregnadiene-17α-ol-17-aromatic heterocyclic carboxylates, and 1,2,-dihydro and 6-dehydro analogs, pharmaceutical formulations thereof, and their use in the treatment and control of inflammatory conditions.

In particular this invention relates to novel 3,20-dioxo-1,4-pregnadiene-17α,21-diol 17-aromatic heterocyclic carboxylates and 21-halogeno-3,20-dioxo-1,4-pregnadiene-17α-ol 17-aromatic heterocyclic carboxylates, particularly 16-methyl derivatives thereof, to pharmaceutical formulations thereof, and their use in the treatment and control of inflammatory conditions.

DESCRIPTION OF THE COMPOSITION-OF-MATTER ASPECT OF THE INVENTION

The composition-of-matter aspect of this invention resides in the concept of a 3,20-dioxo-1,4-pregnadiene-17α-ol 17-aromatic heterocyclic carboxylate having corticoid activity, particularly 16-methyl-3,20-dioxo-1,4-pregnadiene-17α-ol 17-aromatic heterocyclic carboxylates useful as anti-inflammatory agents.

Typical 17-aromatic heterocyclic carboxylates of this invention include 3,20-dioxo-1,4-pregnadienes of the following formula I:

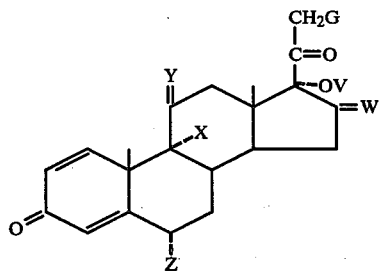

wherein
X is a member selected from the group consisting of hydrogen and halogen having an atomic weight less than 100;
Y is a member selected from the group consisting of (H,H) provided X is hydrogen, oxygen, (H,βOH, and (H,β-halogen) provided X is chlorine or bromine, said β-halogen having an atomic weight of less than 100, and being at least as electronegative as X;
Z is hydrogen, $CH_3$, chlorine, or fluorine;
V is an acyl radical of an aromatic heterocyclic carboxylic acid selected from the group consisting of thiophenecarboxylic acid, pyrrolecarboxylic acid and furancarboxylic acid, and methyl and halogen-substituted derivatives thereof;
W is a member selected from the group consisting of (H,H); (H, lower alkyl); (H, $OV_1$) wherein $V_1$ is a member selected from the group consisting of hydrogen and an acyl radical of an acid selected from the group consisting of a hydrocarboncarboxylic acid having up to 12 carbon atoms, benzoic acid substituted by a halogen or methoxy group, retinoic acid, and isonicotinic acid; =CHT wherein T is a member selected from the group consisting of hydrogen, lower alkyl, fluorine, and chlorine;
G is hydrogen, a halogen having an atomic weight less than 100, or $OV_2$ wherein $V_2$ is a member selected from the group consisting of hydrogen, an acyl radical of a hydrocarbon-carboxylic acid having up to 12 carbon atoms, benzoic acid substituted by a halogen or methoxy group, retinoic acid, isonicotinic acid, and the acid radical of phosphoric acid and mono- and dialkali and alkaline earth metal salts thereof;
and the 6-dehydro and 1,2-dihydro analogs of the foregoing.

Lower alkyl groups included with the definition of W and T are those having up to six carbon atoms such as methyl, ethyl, n-propyl, isopropyl, n-butyl, sec-butyl, n-pentyl, isopentyl, n-hexyl, and 2,3-dimethylbutyl.

As used in the specification and claims of this application, the term "acyl" denotes a radical derived from an acid by removal of a hydroxyl group; e.g. acetyl is the acyl radical of acetic acid, benzenesulfonyl is the acyl radical of benzenesulfonic acid, and benzoyl is the acyl radical of benzoic acid.

The term "acid radical" denotes a radical derived from an acid by removal of a hydrogen atom, e.g. phosphate is the acid radical of phosphoric acid.

The acyl radicals of the compounds of this invention as defined by V in formula I hereinabove include those derived from aromatic heterocyclic carboxylic acids, including 2-furancarboxylic acid, 3-furancarboxylic acid, 2-thiophenecarboxylic acid, 3-thiophenecarboxylic acid, 2-pyrrolecarboxylic acid 3-pyrrolecarboxylic acid, and the methyl and halogen-substituted derivatives thereof, such as 5-methyl-2-thiophenecarboxylic acid, N-methyl-2-pyrrolecarboxylic acid, and 5-bromo-2-furancarboxylic acid. Preferred 17-ester groups as defined by OV of formula I are the 17-furoyl and 17-thenoyl esters.

The acyl radicals of the compounds of this invention as defined by $V_1$ and $V_2$ in formula I hereinabove include those derived from hydrocarboncarboxylic acids having up to 12 carbon atoms which may be saturated, unsaturated, straight chain or branched chain, aliphatic, cyclic, cyclic-aliphatic, aromatic, aryl-aliphatic, or alkyl-aromatic, and may be substituted by hydroxy, alkoxy containing from 1 to 5 carbon atoms or by a halogen. Typical ester groups of the 3,20-dioxo-1,4-pregnadiene 17α-ol 17-aromatic heterocyclic carboxylates as defined by $OV_1$ and $OV_2$ of our invention are thus derived from hydrocarboncarboxylic acids such as alkanoic acids exemplified by formic, acetic, propionic, trimethylacetic, butyric, isobutyric, valeric, isovaleric, caproic, tert.-butylacetic, enanthic, caprylic, capric, cyclopentylpropionic, undecylic, lauric, and adamantanecarboxylic acids; substituted alkanoic acids such as phenoxyacetic, trifluoroacetic, and β-chloropropionic acids; aromatic and substituted aromatic acids including benzoic, toluic, p-chlorobenzoic, p-fluorobenzoic, p-methoxybenzoic, and 3',5'-dimethylbenzoic acids; arylalkanoic acids such as phenylacetic, phenylpropionic, and β-benzoylaminoisobutyric acids; unsaturated acids such as acrylic and sorbic acids; and dibasic acids such as succinic, tartaric, phthalic and benzene disulfonic acids.

The halogens at C-9 and C-21 as defined by X and G, respectively, in above formula I are bromine, chlorine, and fluorine.

The alkylidene groups contemplated in the compounds of my invention are preferably lower alkylidenes, i.e. hydrocarbon radicals having preferably up to four carbon atoms including radicals such as methylene, ethylidene, n-propylidene, isopropylidene, n-butylidene, and sec.-butylidene and the like. Also included are halogeno-alkylidenes, e.g. chloromethylene. The 16-lower alkylidene derivatives of this invention (i.e. when W in above formula I is =CHT) are double bonded to the D ring at C-16.

The physical embodiments of the 3,20-dioxo-1,4-pregnadiene-17α-ol 17-aromatic heterocyclic carboxylates of formula I are characterized by being crystalline solids, usually white to off-white in color, which are insoluble in water (with the exception of alkali metal salts of esters such as the hemisuccinate and phosphate esters thereof) and soluble in most organic solvents, particularly in acetone, dioxane, dimethylformamide, and dimethylsulfoxide, although of limited solubility in non-polar solvents such as dialkyl ethers and alkyl hydrocarbons.

In general, the 3,20-dioxo-1,4-pregnadiene-17α-ol-17αaromatic heterocyclic carboxylates of my invention, particularly those of formula I wherein G is hydroxy, halogen, acyloxy, or phosphate exhibit corticosteriod activity. Of those, those which have halogens at both C-9 and C-11 or those which have an oxygen or β-hydroxyl function at C-11 and a halogen or hydrogen at C-9, possess glucocorticoid activity and are particularly valuable as anti-inflammatory agents.

The 17-acyloxy-21-desoxy- derivatives of formula I, while exhibiting anti-inflammatory activity, are more valuable as progestational agents.

Compounds of this invention which are particularly useful as topical anti-inflammatory agents are the 17-furoyl and 17-thenoyl compounds of formula I wherein G is halogeno or OV$_2$. Of these, those compounds substituted at C-16 by a lower alkyl group (particularly a 16-methyl group, e.g. 16α-methyl) exhibit excellent topical anti-inflammatory activity superior to the topical anti-inflammatory activity of the corresponding 17-hydrocarboncarboxylate derivatives of formula I.

Particularly valuable compounds of my invention are 3,20-dioxo-1,4-pregnadiene-17α-ol 17-aromatic heterocyclic carboxylates of the following formula II:

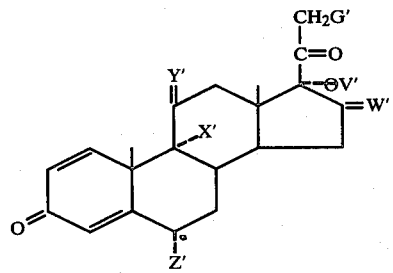

wherein
X' is fluorine or chlorine;
Y' is (H, βOH), or (H, β-halogen) provided X' is chlorine, said β-halogen having an atomic weight of less than 100 and being at least as electronegative as X';
Z' is hydrogen or fluorine;
W' is (H, H) or (H, CH$_3$);
V' is furancarbonyl or thiophenecarbonyl; and
G' is chlorine or OV$_2$', wherein V$_2$' is a member selected from the group consisting of hydrogen, an acyl radical of a hydrocarboncarboxylic acid having up to 12 carbon atoms, benzoic acid substituted by a halogen or methoxy group, retinoic acid, isonicotinic acid, and the acid radical of phosphoric acid and mono- and dialkali and alkaline earth metal salts thereof.

The superior topical activity of the preferred 3,20-dioxo-1,4-pregnadiene-17α-ol 17-aromatic heterocyclic carboxylates of formula II is demonstrated by pharmacological tests in animals. Thus, for example, when tested in mice by a modification of the well-known 5-hour and 5-day croton oil ear edema tests (B. N. Lutsky, et. al., Arzneim.-Forsch. 29, 992, 1979), 9α,11β,21-trichloro-16α-methyl-1,4-pregnadiene-17α-ol-3,20-dione 17-(2'-furoate) exhibits topical potency about twice that of the well known topical anti-inflammatory agent Valisone (i.e. 9α-fluoro-16α-methyl-1,4-pregnadiene-11β,17α,21-triol-3,20-dione 17-valerate) in the 5-hour test, and about eight times the potency in the 5-day test.

In a similar manner, when tested by the above described tests in animals, other 3,20-dioxo-1,4-pregnadiene-17α-ol 17-aromatic heterocyclic carboxylates of formula II, e.g. 9α,21-dichloro-16α-methyl-1,4-pregnadiene-11β,17α-diol-3,20-dione 17-(2'-furoate), 9α-fluoro-16α-methyl-1,4-pregnadiene-11β,17α,21-triol-3,20-dione 17-(2'-furoate) 21-acetate and the corresponding 3'-furoates and 2'-and 3'-thenoates, as well as the 6α-fluoro analogs of the foregoing, exhibit high topical anti-inflammatory activity.

Preferred compounds of formula II include:
the 17-(2'-furoate),17-(3'-furoate),17-(2'-thenoate) and the 17-(3'-theonate) ester derivatives of 9α,21-dichloro-16α-methyl-1,4-pregnadiene-11β,17α-diol-3,20-dione;
the 17-(2'-furoate), 17-(3'-furoate), 17-(2'-thenoate), and the 17-(3'-thenoate) ester derivatives of 9α,11β,21-trichloro-16α-methyl-1,4-pregnadiene-17α-ol-3,20-dione;
the 17-(2'-furoate), 17-(3'-furoate), 17-(2'-thenoate), and the 17-(3'-thenoate) ester derivatives of 9α,11β-dichloro-16α methyl-1,4-pregnadiene-17α,21-diol-3,20-dione 21-acetate;
the 17-(2'furoate), 17-(3'-furoate), 17-(2'-thenoate), and 17-(3'-thenoate) ester derivatives of 9α-fluoro-16α-methyl-1,4-pregnadiene-11β,17α,21-triol-3,20-dione 21-acetate;
the 17-(2'-furoate), 17-(3'-furoate), 17-(2'-thenoate), and 17-(3'-thenoate) ester derivatives of 9α-fluoro-21-chloro-16α-methyl-1,4-pregnadiene-11β,17α-diol-3,20-dione; and
the 6α-fluoro analogs of the above compounds, especially:
6α-fluoro-16α-methyl-1,4-pregnadiene-11β,17α,21-triol-3,20-dione 17-(2'-furoate) 21-acetate,
6α-fluoro-9α,11β-dichloro-16α-methyl-1,4-pregnadiene-17α,21-diol-3,20-dione 17(2'-furoate) 21-acetate,
6α-fluoro-9α,11β,21-trichloro-16α-methyl-1,4-pregnadiene-17α-ol-3,20-dione 17-(2'-furoate), and
6α-fluoro-9α, 21-dichloro-16α-methyl-1,4-pregnadiene-11β,17α-diol-3,20-dione 17-(2'-furoate).

Of the foregoing, particularly valuable are 9α,21-dichloro- 16α-methyl-1,4-pregnadiene-11β,17α-diol-3,20-dione 17-(2'-furoate), and 9α-fluoro-16α-methyl-1,4-pregnadiene-11β,17α,21-triol-3,20-dione 17-(2'-furoate)21-acetate, which have high topical and local anti-inflammatory activity.

Other compounds of formula II include the 16-unsubstituted derivatives of the above compounds, and the 16β-methyl epimers of the same compounds.

In addition to the preferred compounds of formula II, my invention includes 3,20-dioxo-1,4-pregnadiene-17α-ol 17-aromatic heterocyclic carboxylates of formula I such as:

1,4-pregnadiene-11β,17α,21-triol-3,20-dione 17-(2'-furoate) 21-acetate,

16α-methyl-1,4-pregnadiene-11β,17α,21-triol-3,20-dione 17-(2'-furoate) 21-acetate, 1,4,6-pregnatriene-11β,17α,21-triol-3,20-dione 17-(2'-furoate) 21-acetate, 4-pregnene-11β,17α,21-triol-3,20-dione 17-(2'-furoate) 21-acetate, 16α-methyl-1,4-pregnadiene-17α,21-diol-3,20-dione 17-(2'furoate) 21-acetate, 21-desoxy pregnadienes (i.e. compounds of formula I wherein G is hydrogen) such as:

9α,11β-dichloro-16α-methyl-1,4-pregnadiene-17α-ol-3,20-dione 17-(2'-furoate),

9α-fluoro-16α-methyl-1,4-pregnadiene -11β,17α-diol-3,20-dione 17-(2'-furoate),

9α-fluoro-16-methylene-1,4-pregnadiene-11β,17α,21-triol-3,20-dione 17-(2'-furoate) 21-acetate, and 9α-fluoro-1,4-pregnadiene-11β,16α,17α,21-tetrol-3,20-dione 17-(2'-furoate) 16,21-diacetate.

PROCESS OF THE INVENTION

The 3,20-dioxo-1,4-pregnadiene-17α-ol 17-aromatic heterocyclic carbonoyloxy esters are prepared either by direct esterification of the 17α-ol-21-ester or by a method involving a 17,21-orthoester intermediate in which usually all the functional groups desired in the final compound are present in the starting compound.

The 3,20-dioxo-1,4 pregnadiene-17α-ol 17-furoates, 17-thenoates, and 17-pyrrolecarboxylates are conveniently prepared by the direct esterfication by the corresponding heterocyclic carboxoyl chloride or heterocyclic carboxoyl anhydride of 3,20-dioxo-1,4-pregnadiene-17α- ol and a 4-substituted pyridine such as 4-pyrrolidinopyridine or a 4-dialkylaminopyridine, preferably 4-dimethylaminopyridine, in a non-reactive organic solvent.

The direct esterification process is preferably carried out under anhydrous conditions to minimize side reactions such as hydrolysis of any esters present. A preferred ratio of reactants is represented by 1 mole of steriod, 2 moles of heterocyclic carboxoyl chloride, and 10 moles of dimethylaminopyridine. The reaction is preferably carried out at room temperature, that is approximately 20° C. The reaction time varies from 24 to 120 hours, depending on the particular reactants.

Solvents suitable for use in this process are any nonreactive organic solvents in which the starting 3,20-dioxo-1,4-pregnadiene-17α-ol and the aromatic heterocyclic carboxoyl chloride are soluble. By "non-reactive" is meant any organic solvent which will not react with the steroid substrate or the heterocyclic carboxoyl chloride which would cause transformations resulting in competing side reactions. Thus, in our process, solvents to be avoided are water (which will cause hydrolysis of esters) and alcohols (which might cause ester exchange under acid conditions).

Particularly useful solvents for the direct esterification process are methylene chloride, acetonitrile, tetrahydrofura, pyridine, and dimethylformamide. Methylene chloride is particularly preferred as a solvent.

The techniques used to recover the esterified compound from the reaction mixture vary slightly according to the particular reactants, but are well known in the art and are specifically described in the examples.

To prepare 11β-hydroxy 17-esters, it is preferable first to prepare the 17-ester of the 11-oxo compound, then to reduce the 11-oxo to 11β-hydroxy with sodium borohydride using known techniques.

In preparing 21-halogeno compounds of this invention, it is preferable to prepare first the 17-aromatic heterocyclic carboxylate of the corresponding 17-hydroxy 21-alkanoate, then to hydrolyze the 21-alkanoate, e.g. with perchloric acid, followed by reaction with mesyl chloride to produce the 21-mesylate, and finally to replace the mesylate with halogen, using, for example, lithium chloride in a solvent such as dimethylformamide to prepare the 21-chloro compound.

A preferred method for preparing 9α,11β,21-trihalogeno compounds is accomplished by esterifying the 17-hydroxy group of a 9(11)-dehydro 21-alkanoate and converting the resulting 9(11)-dehydro 17-heterocyclic carboxylate 21-alkanoate to the 21-hydroxy with perchloric acid. The 21-hydroxy compound is then converted to the 21-mesylate with mesyl chloride, followed by replacement of the mesylate with halogeno, e.g. via lithium chloride. The resulting 9(11)-dehydro intermediate is then treated with, for example, chlorine in carbon tetrachloride in an amine such as pyridine to produce the desired 9α,11β,21-trihalogeno compound.

9α-Halogeno-11β-hydroxy compounds, in particular 9α-chloro-11β-hydroxy compounds, of the invention may be prepared from a corresponding 9(11)-dehydro starting material by reaction with a suitable halogenating agent such as N-chloro-amide, preferably 1,3-dichloro-5,5-dimethylhydantoin, and a strong mineral acid, preferably perchloric acid, in an inert organic solvent such as moist dioxan or tetrahydrofuran.

Alternatively, the 9α-halogeno-11β-hydroxy compounds of the general formula I may be prepared by treating a corresponding 9α,11β-oxido-starting compound with hydrogen chloride or hydrogen fluoride in a suitable inert solvent. Thus, for instance, the 9α-chloro-11β-hydroxy compounds of the general formula I (which represent a preferred group of compounds) may be prepared by treating a corresponding 9α,11β-oxido-compound, preferably at room temperature, with anhydrous hydrogen chloride in a suitable inert medium, such as glacial acetic aid.

As an alternative to direct esterification, 3,20-dioxo-1,4-pregnadiene-17α,21-diols may be converted to the corresponding 17α,21-heterocyclicorthoesters and then treated with acid to obtain the 17α,21-diol 17-heterocyclic carboxylates, or treated with a triarylsilyl halide to obtain the 21-halogeno-17α-ol 17-heterocyclic carboxylates.

The 17α,21-diol 17-heterocyclicorthoesters are prepared by the known reaction of the corresponding 17α,21-diol with a trialkyl heterocyclicorthoester such as 2-trimethylorthothenoate, 2-trimethylorthofuroate, or 2-trimethylorthopyrroloate in an organic solvent (e.g. a dioxane-benzene mixture) in the presence of a catalyst (e.g. pyridinium p-toluenesulfonate). The reaction is carried out at reflux temperature for 2 to 24 hours.

The resulting 17α,21-diol 17-heterocyclicorthoester may be treated with an acid such as acetic acid and water at room temperature for 24 hours to obtain the desired 17α,21-diol 17-heterocyclic carboxylate, as described in Example 11.

The 21-halogeno-17α-ol 17-heterocyclic carboxylate is prepared by the known reaction of the 17α,21-heterocyclicorthoester with a triarylsilyl halide such as tritolylsilyl or triphenylsilyl halide, or a tri-lower alkylsilyl halide such as trimethylsilyl halide. Preferred halides are the chloride and bromide, with trimethylsilyl chloride being most preferred.

THE METHOD OF USE AND PHARMACEUTICAL FORMULATION ASPECTS OF THE INVENTION

The present invention includes within its scope the method of treating an inflammatory condition in a warm-blooded animal responsive to treatment with anti-inflammatory agents which comprises administering to said animal a non-toxic, anti-inflammatory effective amount of a 3,20-dioxo-1,4-pregnadiene 17-aromatic heterocyclic carboxylate of formula I.

In general, the pharmacologically active 3,20-dioxo-1,4-pregnadiene 17-aromatic heterocyclic carboxylates of formula I, particularly the 17-furoate and 17-thenoate derivatives, have pharmacological effects similar to those of the corresponding 17-alkanoates and may be administered in similar pharmaceutical forms and for the same indications for which the corresponding 3,20-dioxo-1,4-pregnadiene 17-alkanoates would be applicable, the total daily dosage depending upon the nature and severity of the inflammation being treated, the age and size of the patient and the specific potency of the 3,20-dioxo-1,4-pregnadiene 17-aromatic heterocyclic carboxylate being administered.

In particular, the 3,20-dioxo-1,4-pregnadiene 17-aromatic heterocyclic carboxylates of formula I and more particularly, the preferred compounds of formula II, are valuable anti-inflammatory agents when administered topically or locally, since they have high anti-inflammatory action coupled with low gluocorticoid action on topical administration.

The 3,20-dioxo-1,4-pregnadiene 17-aromatic heterocyclic carboxylates may be applied topically or locally in any of the conventional pharmaceutical forms. For example, they may be administered topically in creams, lotions, aerosols or ointments in the treatment of all corticosteriod responsive dermatoses such as contact and allergic dermatitis, eczemas, and psoriasis, or in the form of ophthalmic suspensions or nasal sprays. Advantageously, when topically administering preferred compounds of our invention, i.e. 3,20-dioxo-1,4-pregnadiene 17-furoates and 17-thenoates of formula II, and particularly the 9α,21-chloro-11β-hydroxy derivatives thereof, the therapeutic topical dosages will generally be lower than those required when administering the corresponding 17-alkanoate analog. Thus, a preferred mode of the method-of-use aspect of our invention comprises the method of treating a topical inflammatory condition, e.g. inflammation of the skin or mucous membrane, which comprises topically applying to the affected area in a concentration effective for the topical treatment of inflammation a 3,20-dioxo-1,4-pregnadiene 17-aromatic heterocyclic carboxylate of formula II in association with a pharmaceutical carrier.

Also within the scope of my invention are pharmaceutical compositions for use in the treatment of inflammation comprising an effective amount of novel 3,20-dioxo-1,4-pregnadiene 17-aromatic heterocyclic carboxylate of formula I in association with a compatible, pharmaceutically acceptable carrier or coating. Of the foregoing, preferred are pharmaceutical compositions for topical administration comprising the 3,20-dioxo-1,4-pregnadiene 17-furoates and 17-thenoates of formula II of which the 9α,21-dichloro-11β-hydroxy and 9α-fluoro-11βhydroxy derivatives and the 6α-fluoro analogs thereof, particularly those having a 16α-methyl group, are of greatest value as topical anti-inflammatories.

The pharmaceutical dosage forms are prepared according to procedures well known in the art and may contain other active ingredients, e.g. neomycin sulfate in cream for topical use.

The active steroid may be formulated into a preparation suitable for topical administration in a conventional manner with the aid of one or more carriers or excipients. Examples of types of preparation include ointments, lotions, creams, sprays, powders, drops (e.g. ear drops and eye drops), suppositories or retention enemas (e.g. for the treatment of rectal or colonic inflammations) and aerosols. Ointments and creams may, for example, be formulated with an aqueous or oily base with the addition of suitable thickening and/or gelling agents. Such bases may thus, for example, include water and/or an oil such as liquid paraffin or a vegetable oil such as peanut oil or castor oil. Thickening agents which may be used according to the nature of the base include soft paraffin, aluminum stearate, cetostearyl alcohol, polyethylene glycols, woolfat, hydrogenated lanolin, beeswax, etc.

Lotions may be formulated with an aqueous or oily base and will in general also include one or more of the following, namely, stabilizing agents, emulsifying agents, dispersing agents, suspending agents, thickening agents, coloring agents, perfurmes and the like.

Powders may be formed with the aid of any suitable powder base, e.g. talc, lactose, starch, etc. Drops may be formulated with an aqueous base or non-aqueous base also comprising one or more dispersing agents, suspending agents, solubilizing agents, etc.

The pharmaceutical compositions according to the invention may also include one or more preservatives or bacteriostatic agents, e.g. methyl hydroxybenzoate, propyl hydroxybenzoate, chlorocresol, benzalkonium chlorides, etc.

The compositions according to the invention may also contain other active ingredients such as antimicrobial agents, particularly antibiotics.

The proportion of active steroid in the compositions according to the invention depends on the precise type of formulaions to be prepared but will generally be within the range of from 0.0001% to 5% by weight. Generally, however, for most types of preparations advantageously the proportion used will be within the range of from 0.001 to 0.5% and preferably 0.01 to 0.25%.

The following illustrate topical formulations prepared in accordance with our invention. In each, the active ingredient is denoted by the term "Drug" which represents:

(a) 9α,21-dichloro-16α-methyl-1,4-pregandiene-11β,17α-diol-3,20-dione 17-(2'-furoate),
(b) 9α-fluoro-16α-methyl-1,4-pregnadiene-11β,17α,21-triol-3,20-dione 17-(2'furoate) 21-acetate, and
(c) 9α,11β,21-trichloro-16α-methyl-1,4-pregnadiene-17α-ol-3,20-dione 17-(2'-furoate).

It will be appreciated, however, that these compounds may be replaced by equivalent quantities of other active compounds of this invention.

FORMULATIONS

| 1. Glycol Ointment | mg/g |
|---|---|
| Drug | 0.1–5.0 |
| Hexylene Glycol | 100.0 |
| Propylene Glycol Monostearate | 20.0 |
| White Wax | 60.0 |
| White Petrolatum to make | 1.00 g |

Melt and heat together to 60°–65° C. the propylene glycol monostearate, white wax and white petrolatum. Heat the hexylene glycol to 40° C. and dissolve the drug in it. Add the solution of the hexylene glycol to the above oily phase (cooled to 55° C.) with agitation. Start cooling and continue to agitate until the temperature reaches 30° C.

| 2. Lotion | mg/g |
|---|---|
| Drug | 0.1–5.0 |
| Ethyl Alcohol | 400.0 |
| Polyethylene Glycol 400 | 300.0 |
| Hydroxypropyl Cellulose | 5.0 |
| Propylene Glycol to make | 1.0 g |

Dissolve the drug in the mixture of the ethyl alcohol, polyethylene glycol and propylene glycol. Slowly add the hydroxypropyl cellulose and continue to agitate until the hydroxypropyl cellulose is completely dispersed and wetted and a clear lotion is produced.

| 3. Cream | mg/g |
|---|---|
| Drug | 0.1–5.0 |
| Isopropyl Palmitate | 100.0 |
| Glyceryl Stearate | 80.0 |
| Promulgen-Type D (Robinson, Wagner Co.) | 50.0 |
| White Wax | 50.0 |
| Propylene Glycol | 100.0 |
| Purified water to make | 1.00 g |

Melt together and heat to 75° C. the white wax, glyceryl stearate, Promulgen-Type D and a portion of the isopropyl palmitate and maintain the temperature. Disperse the drug in the remaining portion of the isopropyl palmitate and mill the dispersion. While agitating add the dispersion to the above oily phase. Heat together the water and the propylene glycol to 75° C. Add the solution to the above oily phase with agitation. Start cooling and continue to agitate until the temperature reaches 30° C.

| 4. Topical Aerosol | mg/can |
|---|---|
| Drug | 6.4 |
| Mineral Oil | 1,250.0 |
| Neobee M-5 (Caprylic/Capric Glyceride) (PVO International, Inc.) | 3,743.6 |
| Dichlorodifluoromethane | 17,200.0 |
| Trichloromonofluoromethane | 68,800.0 |
| | 91,000.0 |

Dissolve the drug in Neobee M-5 and add mineral oil. Place this concentrate into an aerosol and crimp a valve on the can. Inject the dichlorodifluoromethane and trichloromonofluoromethane mixture into the container through the valve.

The processes described hereinabove are illustrated in detail in the Examples hereinbelow and should not be construed as limitating the invention, equivalents thereof and products produced thereby which will be obvious to one skilled in the art being considered a part of the invention.

The molecular structure of the compounds of the invention described in detail hereinabove were assigned on the basis of their method of preparation and study of their chromatographic characteristics and of their neclear magnetic resonance (nmr), mass spectra and ultraviolet spectra, and were confirmed by the correspondence between calculated and found values of elementary analyses for the elements.

EXAMPLE 1

9α,11β-DICHLORO-16-METHYL-1,4-PREGNADI-
ENE-17α,21-DIOL-3,20-DIONE
17-HETEROCYCLIC CARBOXYLATE
21-ALKANOATES (A)

9α,11β-Dichloro-16α-Methyl-1,4-Pregnadiene-17α,21-Diol-3,20-Dione 17-(2'-Furoate) 21-Acetate Dissolve 4-dimethylaminopyridine (12 gms.), 9α,11β-dichloro-16α-methyl-1,4-pregnadiene-17α,21-diol-3,20-dione 21-acetate (4.8 gms.), and 2-furoyl chloride (2 ml.) in methylene chloride (62 ml.) and stir at room temperature until thin-layer chromatography of an aliquot of the mixture indicates no more of the desired product is being formed. Evaporate the reaction mixture, add an excess of dilute hydrochloric acid to the resultant residue, stir for 30 minutes and collect the insolubles. Add an excess of dilute sodium carbonate, stir for 30 minutes, collect the solids, wash with water, and dry at 60° C. to obtain 9α,11β-dichloro-16α-methyl-1,4-pregnadiene-17α,21-diol-3,20-dione 17-(2'-furoate) 21-acetate.

Purify the crude product by recrystallizing from methylene chloride (75 ml.)/ether (300 ml.). Further purify by clarifying a methylene chloride solution of this recrystallized product by gravity filtration through charcoal (Darco G-60), then again crystallizing the product by adding ether (200 ml.) to the methylene chloride solution (adjusted to 45 ml. after Darco treatment) and concentrating to 200 ml. Add an additional 50 ml. of ether, filter the crystals, and dry at 45° C. under vacuum to obtain the purified product.

(B)

9α,11β-Dichloro-16α-Methyl-1,4-Pregnadiene-17α,21-Diol-3,20-Dione 17-(2'-furoate) 21-Acetate Treat 9α,11β-dichloro-16α-methyl-1,4-pregnadiene-17α,21-diol-3,20-dione 21-acetate in a manner similar to that described in Example 1A, first paragraph, to obtain the title compound.

Purify the crude product by preparative thin-layer chromatography on silica gel, using chloroform:ethyl acetate (19:1) as the developing solvent. Visualize the desired band by ultraviolet light, remove the band, and elute with ethyl acetate. Evaporate the solvent and crystallize from methylene chloride: ether to obtain purified 9α,11β-dichloro-161,4-pregnadiene-17α,21-diol-3,20-dione 17-(2'-furoate) 21-acetate.

(C)
9α,11β-Dichloro-16α-Methyl-1,4-Pregnadiene-17α,21-Diol-3,20-Dione 17-Heterocyclic Carboxylate 21-Acetate Similarly, by substituting 3-furoyl chloride, 2-thenoyl chloride, and 5-bromo-2-furoyl chloride for 2-furoyl chloride in Example 1A, first paragraph, there are obtained 9α,11β-dichloro-16α-methyl-1,4-pregnadiene-17α,21-diol-3,20-dione 17-(3'-furoate) 21-acetate; 9α,11β-dichloro-16α-methyl-1,4-pregnadiene-17α,21-diol-3,20-dione 17-(2'-thenoate) 21-acetate, and 9α,11β-dichloro-16α-methyl-1,4-pregnadiene-17α,21-diol-3,20-dione 17-(2'-(5'-bromofuroate)) 21-acetate.

Purify each product by the preparative thin-layer chromatographic method described in Example 1B, second paragraph, and crystallize each of the resultant residues from ethyl acetate:hexane, methylene chloride:hexane, and ethyl acetate:hexane, respectively.

(D)
9α,11β-Dichloro-16α-Methyl-1,4-Pregnadiene-17α,21-Diol-3,20-Dione 17-(2'-Furoate) 21-Propionate Treat 9α,11β-dichloro-16α-methyl-1,4-pregnadiene-17α,21-diol-3,20-dione 21-propionate with 2-furoyl chloride in the manner of Example 1A, first paragraph, to obtain the title compound.

Purify the resultant crude product as in Example 1B, second paragraph, to obtain purified 9α,11β-dichloro-16α-methyl-1,4-pregnadiene-17α,21-diol-3,20-dione 17-(2'-furoate) 21-propionate.

EXAMPLE 2
9α,11β,21-TRICHLORO-16-METHYL-1,4-PREGNADIENE-17α-OL-3,20-DIONE 17-HETEROCYCLIC CARBOXYLATES

(A)
16-Methyl-1,4,9(11)-Pregnatriene-17α,21-Diol-3,20-Dione 17-Heterocyclic Carboxylate 21-Acetates (1) Dissolve 16α-methyl-1,4,9(11)-pregnatriene-17α,21-diol-3,20-dione 21-acetate (9.96 gms, 25 mmols), 2-furoyl chloride (4.95 ml., 50 mmols), and 4-dimethylaminopyridine (30.35 gms., 250.0 mmols) in methylene chloride (150 ml.) and stir at room temperature until thin-layer chromatography of an aliquot of the reaction mixture indicates no more product is being formed. Evaporate the mixture to a residue, and treat the residue with dilute hydrochloric acid and sodium carbonate as in Example 1A. Dissolve the collected insolubles in acetone (300 ml.) and add to a saturated sodium chloride solution to precipitate 16α-methyl-1,4,9(11)-pregnatriene-17α,21-diol-3,20-dione 17-(2'-furoate) 21-acetate.

Purify via chromatography on silica gel, eluting with chloroform:ethyl acetate (9:1). Combine the like fractions as determined by thin-layer chromatography and evaporate to obtain the purified product.

(2) Treat 16β-methyl-1,4,9(11)-pregnatriene-17α,21-diol-3,20-dione 21-acetate in the manner of Example 2A(1) to obtain 16β-methyl-1,4,9(11)-pregnatriene-17α,21-diol-3,20-dione 17-(2'-furoate) 21-acetate.

(3) Substitute 3-furoyl chloride and 2-thenoyl chloride for 2-furoyl chloride in Example 2A(1) to obtain 16α-methyl-1,4,9(11)-pregnatriene-17α,21-diol-3,20-dione 17-(3'-furoate) 21-acetate and 16α-methyl-1,4,9(11)-pregnatriene-17α,21-diol-3,20-dione 17-(2'-thenoate) 21-acetate, respectively.

(B)
16-Methyl-1,4,9(11)-Pregnatriene-17α,21-Diol-3,20-Dione 17-Heterocyclic Carboxylates (1) To a suspension of the compound prepared in Example 2A(1) (4.46 gms) in methanol (125 ml.) at room temperature, add 70% perchloric acid (4.9 ml.), dropwise. Let stand overnight. Filter any insolubles; add the filtrate to a saturated sodium chloride solution and collect the insolubles. Combine the solids and dry at 45° C. to obtain 16α-methyl-1,4,9(11)-pregnatriene-17α,21-diol-3,20-dione 17-(2'-furoate).

(2) Hydrolyze each of the 17-heterocarboxylate 21-acetates of Example 2A(2) and (3) in a similar manner to obtain the corresponding 17-heterocyclic carboxylate 21-hydroxy compounds.

(C)
16-Methyl-1,4,9(11)-Pregnatriene-17α,21-Diol-3,20-Dione 17-Heterocyclic Carboxylate 21-Mesylates (1) To a solution of the compound prepared in Example 2B(1) (3 gms.) in pyridine (43 ml.) cooled to 0°–2° C., add dropwise mesyl chloride (5.1 ml.) and let stand for one hour. Pour the reaction mixture into ice water, collect and dry the resultant precipitate to obtain 16α-methyl-1,4,9(11)-pregnatriene-17α, 21-diol-3,20-dione 17-(2'-furoate) 21-mesylate.

(2) To a solution of the 16β-methyl compound prepared in Example 2B(2) (0.361 gms.) in pyridine (4 ml.) cooled to 0°–5° C., add dropwise mesyl chloride (0.62 ml.) and let stand for one hour. Pour the reaction mixture into a saturated sodium chloride solution, collect the resultant precipitate and dry at 60° C. to obtain 16β-methyl-1,4,9(11)-pregnatriene-17α,21-diol-3,20-dione 17-(2'-furoate) 21-mesylate.

(3) Treat each of the 17-(3'-furoate) and 17-(2'thenoate) compounds prepared in Example 2B(2) in a manner similar to that described in Example 2C(1) to obtain the corresponding 17-heterocyclic carboxylate 21-mesylates.

(D)
21-Chloro-16-Methyl-1,4,9(11)-Pregnatriene-17α-Ol-3,20-Dione 17-Heterocyclic Carboxylates (1) Stir the product of Example 2C(1) (3.4 gms.) and lithium chloride (3.4 gms.) in dimethylformamide (51 ml.) at 80° C. for 9 hours. Add the reaction mixture to a saturated sodium chloride solution, collect and dry the resultant precipitate at 50° C. to obtain 21-chloro-16α-methyl-1,4,9(11)-pregnatriene-17α-ol-3,20-dione 17-(2'-furoate).

(2) Treat the product of Example 2C(2) in a similar manner to that described in Example 2D(1) to obtain 21-chloro-16β-methyl-1,4,9(11)-pregnatriene-17α-ol-3,20-dione 17-(2'-furoate). Purify the foregoing product by preparative thin-layer chromatography on silica gel using chloroform:ethyl acetate (19:1) as developing solvent. Visualize the desired band with ultraviolet light, remove the band and elute with ethyl acetate. Evaporate the solvent to obtain the purified product.

(3) Treat each of the compounds prepared in Example 2C(3) in a manner similar to that described in Example 2D(1).

Purify the resulting crude 21-chloro-16α-methyl-1,4,9(11)-pregnatriene-17α-ol-3,20-dione 17-(3'-furoate) by crystallizing from methylene chloride:hexane, followed by preparative thin-layer chromatography using chloroform:ethyl acetate (8:1) as the developing solvent.

Purify the crude 21-chloro-16α-methyl-1,4,9(11)-pregnatriene-17α-ol-3,20-dione 17-(2'-thenoate) as in Example 2D(2), second paragraph.

(E)
9α,11β,21-Trichloro-16-Methyl-1,4-Pregnadiene-17α-Ol-3,20-Dione 17-Heterocyclic Carboxylate (1) To a solution of the product of Example 2D(1) (2.3 gms, 4.0 mmols) and pyridine hydrochloride (1.42 gms) in methylene chloride (37 ml.) at −35° C. to −40° C. add carbon tetrachloride containing chlorine (3.26 ml; 128 mgs. Cl₂ per milliliter) and stir for 20 minutes. Evaporate the solvent, add water to the resultant residue, and collect the insolubles to obtain 9α,11β,21-trichloro-16α-methyl-1,4-pregnadiene-17α-ol-3,20-dione 17-(2'furoate).

Purify the product by crystallization from methylene chloride:ether, followed by preparative thin-layer chromatography on silica gel using chloroform:ethyl acetate (9:1) as the developing solvent. Visualize the desired band with ultraviolet light, remove the band and elute with ethyl acetate. Evaporate the solvent to obtain the purified product.

(2) In a manner similar to that described in Example 2E(1), treat each of the products of Example 2D(2), (3) and (4) with chlorine in carbon tetrachloride to obtain the corresponding 9α,11β,21-trichloro-17-heterocyclic carboxylates, i.e., 9α,11β,21-trichloro-16α-methyl-1,4-pregnadiene-17α-ol-3,20-dione 17-(2'-furoate); 9α,11β,21-trichloro-16α-methyl-1,4-pregnadiene-17α-ol-3,20-dione 17-(3'-furoate); and 9α,11β,21-trichloro-16α-methyl-1,4-pregnadiene-17α-ol-3,20-dione 17-(2'-thenoate).

EXAMPLE 3

9α-FLUORO-16-METHYL-1,4-PREGNADIENE-11β,17α,21-TRIOL-3,20-DIONE 17-HETEROCYCLIC CARBOXYLATES (A)
9α-Fluoro-16-Methyl-1,4-Pregnadiene-17α,21-Diol-3,11,20-Trione 17-Heterocyclic Carboxylate 21-Acetates (1) To a solution of 4-dimethylaminopyridine (8.4 gms., 70 mmols) in methylene chloride (42 ml.), add dropwise 2-furoyl chloride (1.8 ml., 18.2 mmols) with stirring. Add 9α-fluoro-16α-methyl-1,4-pregnadiene-17α,21-diol-3,11,20-trione 21-acetate (3 gms., 6.9 mmols) and stir at room temperature until thin-layer chromatography of an aliquot of the reaction mixture indicates no more product is being formed. Evaporate the reaction mixture and treat the resultant residue by successive trituration with dilute hydrochloric acid and dilute sodium carbonate; collect the insolubles, wash with water, and dry under vacumm at 40° C. to obtain 9α-fluoro-16α-methyl-1,4-pregnadiene-17α,21-diol-3,11,20-trione 17(2'-furoate) 21-acetate.

Purify the crude product via preparative thin-layer chromatography on silica gel: develop the plates twice in chloroform:ethyl acetate (40:1), visualize the desired band by ultraviolet light, remove the band and elute with ethyl acetate. Evaporate the eluate to a residue to obtain purified 9α-fluoro-16α-methyl-1,4-pregnadiene-17α,21-diol-3,11,20-trione 17-(2'-furoate) 21-acetate.

(2) In the procedure of Example 3A(1), substitute for 2-furoyl chloride equivalent amounts of 3-furoyl chloride and 2-thenoyl chloride to obtain 9α-fluoro-16α-methyl-1,4-pregnadiene-17α,-21-diol-3,11,20-trione 17-(3'-furoate) 21-acetate and 9α-fluoro-16α-methyl-1,4-pregnadiene-17α-21-diol-3,11,20-trione 17-(2'-thenoate) 21-acetate, respectively.

(3) Treat 9α-fluoro-16β-methyl-1,4-pregnadiene-17α, 21-diol-3,11,20-trione 21-acetate in a manner similar to that described in Example 3A(1), first paragraph, but substitute dimethylformamide:methylene chloride (1:1) for methylene chloride.

Purify the crude 9α-fluoro-16β-methyl-1,4-pregnadiene-17α, 21-diol-3,11,20-trione 17-(2'-furoate) 21-acetate as in Example 3A(1), second paragraph, followed by a second preparative thin-layer chromatographic purification using hexane:ethyl acetate (2:1) as the developing solvent.

(B)
9α-Fluoro-16-Methyl-1,4-Pregnadiene-11β-17α,21-Triol-3,20-Dione 17-Heterocyclic Carboxylate 21-Acetate (1) To a solution of the compound prepared in Example 3A(1) (0.986 gms., 1.866 mmols) in dimethylformamide (26 ml.), methanol (30 ml.), and water (3 ml.) cooled to 0°–2° C. and under an atmosphere of nitrogen, add solid sodium borohydride (0.212 gms., 5.56 mmols.). After 20 minutes, add 1 N hydrochloric acid (6 ml.), wait 1 minute, and pour the reaction mixture into a saturated sodium chloride solution (600 ml.). Collect the precipitate and dry at 60° C.

Purify the crude product by preparative thin-layer chromatography on silica gel, using chloroform:ethyl acetate (9:1) to develop the plates. Visualize the desired band by ultraviolet light, remove the band, and elute with ethyl acetate. Evaporate the solvent and crystallize the resultant residue from methylene chloride:ether to obtain 9α-fluoro-16α-methyl-1,4-pregnadiene-11β,17α,21-triol-3,20-dione 17-(2'-furoate) 21-acetate.

(2) In the procedure of Example 3B(1) first paragraph, substitute the products of Example 3A(2) for the 17-(2'-furoate) substitute argon for nitrogen, and run at 0°–5° C. to obtain 9α-fluoro-16α-methyl-1,4-pregnadiene-11β,17α,21-triol-3, 20-dione 17-(3'-furoate) 21-acetate and 9α-fluoro-16α-methyl-1, 4-pregnadiene-11β,17α,21-triol-3,20-dione 17-(2'-thenoate) 21-acetate, respectively.

Purify the crude 17-(3'-furoate) and 17-(2'-thenoate) by preparative thin-layer chromatography as in Example 3B(1), second paragraph, substituting chloroform:ethyl acetate at ratios of (19:1) and (13:1) for the developing solvents, respectively.

(3) To a solution of the compound prepared in Example 3A(3) (26 mgs., 0.0494 mmols.) in methanol (2.5 ml.) and water (0.3 ml.) cooled to 0°–5° C. and under a nitrogen atmosphere, add sodium borohydride (7 mgs., 0.148 mmols.). After 20 minutes, add to dilute hydrochloric acid and extract with ethyl acetate to obtain 9α-fluoro-16β-methyl-1,4-pregnadiene-11β,17α,21-triol-3,20-dione 17-(2'-furoate) 21-acetate.

Purify the crude product using preparative thin-layer chromatography as in Example 3B(1), second paragraph, substituting chloroform:ethyl acetate (19:1) for the developing solvent.

(C)
9α-Fluoro-16-Methyl-1,4-Pregnadiene-11β,17α,21-Triol-3,20-Dione 17-Heterocyclic Carboxylates (1) To a suspension of the compound prepared in Example 3B(1) (334 mgs., 0.634 mmols.) in methanol (9 ml.) under an atmosphere of nitrogen, add with stirring 70% perchloric acid (0.34 ml.). After 18 hours separate the insolubles and add the clear reaction mixture to a saturated aqueous sodium chloride solution (150 mls.); collect and dry the precipitate at 60° C. to obtain 9α-fluoro-16α-methyl-1,4-pregnadiene-11β,17α,21-triol-3,20-dione 17-(2′-furoate).

(2) Treat the compound prepared in Example 3B(3) in a manner similar to that described in Example 3C(1) to obtain 9α-fluoro-16β-methyl-1,4-pregnadiene-11β,17α,21-triol-3,20-dione 17-(2′-furoate).

Purify the crude product by crystallization from ethyl acetate:hexane, then by preparative thin-layer chromatography in the usual manner, using chloroform:ethyl acetate (4:1) as developing solvent.

(3) In the procedure of Example 3C(1) substitute for the 17-(2′-furoate) equivalent amounts of 17-(3′-furoate) and 17-(2′-thenoate) to obtain the corresponding 9α-fluoro-16α-methyl-1,4-pregnadiene-11β,17α,21-triol-3,20-dione 17-(3′-furoate) and 9α-fluoro-16α-methyl-1,4-pregnadiene-11β, 17α,21-triol-3,20-dione 17-(2′-thenoate).

(D)
9α-Fluoro-16α-Methyl-1,4-Pregnadiene-11β,17α,21-Triol-3,2,-Dione 17-(2′-Furoate) 21-Propionate (1) To a solution of the compound of Example 3C(1) (0.1 gms., 0.021 mmols.) in pyridine (3 ml.) cooled to 0°-2° C., add propionyl chloride (0.3 ml., 0.035 mmols.). After 17 hours, add to dilute hydrochloric acid and extract with ethyl acetate. Evaporate the ethyl acetate extract to give a residue comprising 9α-fluoro-16α-methyl-1,4-pregnadiene-11β, 17α,21-triol-3,20-dione 17-(2′-furoate) 21-propionate.

Purify the crude product by preparative thin-layer chromatography using chloroform:ethyl acetate (8:1) as developing solvent, followed by crystallization from methylene chloride:hexane.

(2) In the procedure of 3D(1), treat the products of Examples 3C(2) and (3) with propionyl chloride to obtain the corresponding 17-heterocyclic carboxylate 21-propionates.

EXAMPLE 4

9α-FLUORO-21-CHLORO-16-METHYL-1,4-PREGNADIENE-11β, 17α-DIOL-3,20-DIONE 17-HETEROCYCLIC CARBOXYLATE (A) 9α-Fluoro-16α-Methyl-1,4-Pregnadiene-11β,17α, 21-Triol-3,20-Dione 17-Hetercyclic Carboxylate 21-Mesylates (1) Dissolve the compound of Example 3C(1) (269 mgs., 0.553 mmols.) in a mixture of mesyl chloride (0.43 ml., 5.53 mmols.) and pyridine (2.75 ml.) maintained at 0°-2° C. After 1 hour, add reaction mixture to a saturated sodium chloride solution. Collect the insoluble material and dry at 40° C. to obtain 9α-fluoro-16α-methyl-1, 4-pregnadiene-11β,17α,21-triol-3,20-dione 17-(2′furoate) 21-mesylate.

(2) In a similar manner to Example 4A(1), treat the compounds prepared in Examples 3C(2) and (3) to obtain the corresponding 17-heterocyclic carboxylate 21-mesylates.

(B) 9α-Fluoro-21-Chloro-16α-Methyl-1, 4-Pregnadiene-11β,17α-Diol-3,20-Dione 17-Heterocyclic Carboxylates (1) Dissolve the compound of Example 4A(1) (279 mgs., 0.494 mmols.) and lithium chloride (350 mgs.) in dimethylformamide (4 ml.) and maintain temperature at 80° C. for 21 hours. Add the reaction mixture to a saturated sodium chloride solution, collect the insolubles and dry at 50° C. to obtain 9α-fluoro-21-chloro-16α-methyl-1,4-pregnadiene-11β, 17α-diol-3,20-dione 17-(2′-furoate).

Purify the product via preparative thin-layer chromatography, using chloroform:ethyl acetate (8:1) as developing solvent. Crystallize the resultant chromatographic extract from methylene chloride:hexane to obtain the purified title compound.

(2) Treat the compounds prepared in Example 4A(2) in the manner of Example 4B(1) to obtain the corresponding 21-chloro 17-heterocyclic carboxylate, i.e., 9α-fluoro-21-chloro-16β-methyl-1,4-pregnadiene-11β, 17αdiol-3,20-dione 17-(2′-furoate), 9α-fluoro-21-chloro-16α-methyl-1, 4-pregnadiene-11β,17α-diol-3,20-dione 17-(3′-furoate), and 9α-fluoro-21-chloro-16α-methyl-1, 4-pregnadiene-11β,17α-diol-3,20-dione 17-(2′-thenoate).

EXAMPLE 5

1,4-PREGNADIENE-11β,17α,21-TRIOL-3,20-DIONE 17-(2′-FUROATE) 21-ACETATE AND THE 9α-FLUORO ANALOG THEREOF (A) 1,4-Pregnadiene-17α,21-Diol--3,11, 20-Trione-17-(2′-Furoate) 21-Acetate Treat 1,4-pregnadiene-17α,21-diol-3,11,20-trione 21-acetate in a manner similar to that described in Example 1A, first paragraph, to obtain the title compound.

Purify the product by successive preparative thin-layer chromatography procedures, the first using chloroform:ethyl acetate (9:1) as developing solvent, the second using hexane:ethyl acetate (2:1).

(B) 1,4-Pregnadiene-11β,17α,21-Triol-3,20-Dione 17-(2′-Furoate) 21-acetate

To a solution of the compound of Example 5A (148 mg.) in methanol (15 ml.), dimethylformamide (10 ml.), and water (1.5 ml.) cooled to 0°-2° C. and under a nitrogen atmosphere, add sodium borohydride (34.1 mgs.). After 20 minutes, add to dilute hydrochloric acid (250 ml.) and collect the insolubles. Extract the aqueous solution with ethyl acetate, evaporate the organic phase and combine the residues to give 1,4-pregnadiene-11β,17α,21-triol-3,20-dione 17-(2′-furoate) 21-acetate.

Purify the crude product by preparative thin-layer chromatography in the usual manner using chloroform:ethyl acetate (4:1) as the developing solvent, followed by crystallizing from methylene chloride:hexane.

(C) 9α-Fluoro-1,4-Pregnadiene-11β,17α,21-Triol-3, 20-Dione 17-(2′-Furoate) 21-Acetate Treat 9α-fluoro-1,4-pregnadiene-17α,21-diol-3, 20-dione 21-acetate with 2-furoyl chloride and purify the product as described in Example 5A. Treat the 17-(2′-furoate) thus prepared with sodium borohydride and purify as described in Example 5B to produce the title compound.

EXAMPLE 6

16-METHYL-1,4-PREGNADIENE-11β,17α,21-TRIOL-3, 20-DIONE 17-(2′-FUROATE) 21-ACETATES

Treat each of 16α-methyl-1,4-pregnadiene-17α, 21-diol-3,11,20-trione 21-acetate and 16β-methyl-1,4-pregnadiene-17α, 21-diol-3,11,20-trione 21-acetate in a manner similar to Example 5A and 5B to obtain the corresponding 16α-methyl-1,4-pregnadiene-11β, 17α,21-triol-3,20-dione 17-(2'-furoate) 21-acetate and 16β-methyl-1,4-pregnadiene-11β, 17α,21-triol-3,20-dione 17-(2'-furoate) 21-acetate.

EXAMPLE 7

9α,11β-DICHLORO-16α-METHYL-1,4-PREGNADIENE-17α, 21-DIOL-3,20-DIONE 17-(5'-METHYL-2'-THENOATE) 21-ACETATE

Dissolve 4-dimethylaminopyridine (3 gms.), 9α, 11β-dichloro-16α-methyl-1,4-pregnadiene-17α, 21-diol-3,20-dione 21-acetate (1 gm.), and 5-methyl-2-thenoyl chloride (0.6 ml.) in methylene chloride (10 ml.) and stir at room temperature until thin-layer chromatography of an aliquot of the mixture indicates no more of the desired product is being formed. Dilute the resultant mixture with methylene chloride (200 ml.), add dilute hydrochloric acid and stir for 45 minutes. Separate the methylene chloride phase, wash with dilute sodium carbonate, then wash with water, and evaporate the organic phase.

Purify the crude product by preparative thin-layer chromatography on silica gel using chloroform:ethyl acetate (40:1) as developing solvent. Visualize the desired band by ultraviolet light, remove the band, and elute with ethyl acetate. Repeat the preparative thin-layer chromatography, developing with chloroform:ethyl acetate (15:1). Elute with ethyl acetate, evaporate the solvent, and recrystallize the resultant residue from methylene chloride:ether to obtain pure 9α,11β-dichloro-16α-methyl-1, 4-pregnadiene-17α,21-diol-3,20-dione 17-(5'-methyl-2'-thenoate) 21-acetate.

EXAMPLE 8

9α-FLUORO-16α-METHYL-1,4-PREGNADIENE-11β,17α, 21-TRIOL-3,20-DIONE 17-(5'-METHYL-2'-THENOATE) 21-ACETATE

Treat 9α-fluoro-16α-methyl-1, 4-pregnadiene-11β,17α,21-triol-3,20-dione 21-acetate in a manner similar to that described in Example 7, first paragraph, but with the addition of 2.5 ml. dimethylformamide, to obtain the title compound.

Purify the crude product by preparative thin-layer chromatography as usual, developing with chloroform:ethyl acetate (50:1). Purify further by preparative thin-layer chromatography using chloroform:ethyl acetate (10:1) as developing solvent and recrystallize the resultant residue from methylene chloride:hexane.

EXAMPLE 9

9α,11β-DICHLORO-16α-METHYL-1,4-PREGNADIENE-17α, 21-DIOL-3,20-DIONE 17-(N-METHYL-2'-PYRROLYL CARBOXYLATE) 21-ACETATE

Dissolve 9α,11β-dichloro-16α-methyl-1, 4-pregnadiene-17α,21-diol-3,20-dione 21-acetate (3 gms.) in methylene chloride (30 ml.) and add 4-dimethylaminopyridine (8.4 gms.) and N-methylpyrrole 2-carboxoyl chloride (2 ml.). Stir at room temperature until thin-layer chromatography of an aliquot of the mixture indicates no more of the desired product is being formed. Evaporate the reaction mixture, add dilute sodium carbonate, and stir 1 hour. Extract the solution three times with 200 ml. methylene chloride, combine the organic phases, wash with water, and evaporate the organic phase to a residue to obtain the title compound.

Purify the crude compound by silica gel chromatography, eluting with ethyl acetate. Combine the like fractions as determined by thin-layer chromatography, and evaporate the solvent to obtain the title compound. Purify further by preparative thin-layer chromatography, using chloroform:ethyl acetate (20:1) as developing solvent. Extract the sample band as usual with ethyl acetate, evaporate, and crystallize the resultant residue from ether to obtain purified title compound.

EXAMPLE 10

6α-FLUORO-16α-METHYL-1, 4-PREGNADIENE-17α-OL-3, 20-DIONE 17-AROMATIC HETEROCYCLIC CARBOXYLATES

A. 6α-Fluoro-16α-Methyl-1, 4-Pregnadiene-11β,17α,21-Triol-3,20-Dione 17-(2'-Furoate) 21-Acetate 1. 6α-Fluoro-16α-Methyl-1, 4-Pregnadiene-17α,21-Diol-3,11,20-Trione 17-(2'-Furoate) 21-Acetate Dissolve 4-dimethylaminopyridine (9 gms.) and 2-furoyl chloride (2.1 ml.) in methylene chloride (40 ml.), add 6α-fluoro-16α-methyl-1, 4-pregnadiene-17α,21-diol-3,11,20-trione 21-acetate (2.9 gms.) in methylene chloride (20 ml.) and stir at room temperature for 96 hours. Dilute the reaction mixture with methylene chloride (300 ml.), then wash with dilute hydrochloric acid. Separate the organic phase, dry over anhydrous sodium sulfate, and evaporate to a residue.

Dissolve the resultant residue in methylene chloride (100 ml.) and filter the solution through neutral aluminum oxide to obtain the purified title compound. Purify further by preparative thin-layer chromatography using ethyl acetate:hexane (1:1) to develop the plates, extracting the band as usual with ethyl acetate, and evaporating the extract to a residue to obtain purified material.

2. 6α-Fluoro-16α-Methyl-1, 4-Pregnadiene-11β,17α, 21-Triol-3,20-Dione 17-(2'-Furoate) 21-Acetate Dissolve the product of Example 10A(1) (0.360 gms.) in dimethylformamide (10 ml.) and methanol (10 ml.). Cool the solution to 0° C., and under a nitrogen atmosphere add sodium borohydride (0.073 gms.). Stir for 30 minutes at 0° C. Add dilute hydrochloric acid (18 ml.) to the reaction mixture and pour the resultant solution into ice water saturated with sodium chloride. Collect the resultant solids and purify by preparative thin-layer chromatography using chloroform:ethyl acetate (2:1) as developing solvent. Extract the product as usual with ethyl acetate, evaporate to a residue, and crystallize from ethyl acetate:hexane (3:1) to obtain the purified title compound.

B. 6α-Fluoro-9α,11β-Dichloro-16α-Methyl-1, 4-Pregnadiene-17α,21-Diol-3,20-Dione 17-(2'-Furoate) 21-Acetates 1. 6α-Fluoro-16α-Methyl-1,4, 9(11)-Pregnatriene-17,21-Diol-3, 20-Dione 21-Acetate Under a nitrogen atmosphere, cool to 0° C. a solution of 6α-fluoro-16α-methyl-1, 4-pregnadiene-11β,17α,21-triol-3,20-dione 21-acetate (12.5 gms.) in dimethylformamide (25 ml.) and collidine (25 ml.). Add slowly methanesulfonyl chloride/$SO_2$ solution (1.41 gms. $CH_3SO_2Cl$/ml.) and stir for 45 minutes at 0° C., then stir at room temperature for 30 minutes. Pour the resultant reaction mixture into ice water (1.1 L.), collect the insolubles and wash with water to obtain the crude title compound. To purify, dissolve the residue in methylene chloride, filter through silica gel, and evaporate the solvent to obtain purified product.

2. 6α-Fluoro-16α-Methyl-1, 4,9(11)-Pregnatriene-17α,21-Diol-3, 20-Dione 17-(2'-Furoate) 21-Acetate Treat the product of Example 10B(1) in a manner similar to that described in Example 2A(1), first paragraph, to obtain the title compound. Purify the crude product as usual by preparative thin-layer chromatography, developing with hexane:ethyl acetate (2:1).

3. 6α-Fluoro-9α, 11β-Dichloro-16α-Methyl-1, 4-Pregnadiene-17α,21-Diol-3,20-Dione 17-(2'-Furoate) 21-Acetate Treat the product of Example 10B(2) in a manner similar to that described in Example 2E(1), substituting hexane:ethyl acetate (2:1) for solvent, and purifying further by crystallizing from methylene chloride:hexane, to obtain the title compound.

C. 6α-Fluoro-9α, 11β,21-Trichloro-16α-Methyl-1, 4-Pregnadiene-17α-01-3,20-Dione 17-(2'-Furoate)

1. 6α-Fluoro-16α-Methyl-1, 4,9(11)-Pregnatriene-17α, 21-Diol-3,20-Dione 17-(2'-Furoate)

Treat the product of Example 10B(2) in a manner similar to that described in Example 2B(1) to obtain the title compound. Purify by preparative thin-layer chromatography as usual, using chloroform:ethyl acetate (9:1) to develop the plates, and hexane:ethyl acetate (2:1) to crystallize the purified title compound.

2. 6α-Fluoro-16α-Methyl-1, 4,9(11)-Pregnatriene-17α, 21-Diol-3,20-Dione 17-(2'-Furoate) 21-Mesylate Dissolve the product of Example 10C(1) (4.4 gms.) in pyridine (30 ml.), add mesyl chloride (5 ml.) cooled to 0°-2° C., and stir 1 hour at room temperture under a nitrogen atmosphere. Pour the reaction mixture into dilute hydrochloric acid (300 ml.), collect and dry the insolubles to obtain the title compound.

3. 6α-Fluoro-21-Chloro-16α-Methyl-1, 4,9(11)-Pregnatriene-17α-OL-3,20-Dione 17-(2'Furoate)

Treat the compound prepared in Example 10C(2) in a manner similar to that described in Example 2D(1) to obtain the title compound.

4. 6α-Fluoro-9α,11β, 21-Trichloro-16α-Methyl-1,4-Pregnadiene-17α-01-3, 20-Dione 17-(2'-Furoate)

Treat the compound prepared in Example 10C(3) in a manner similar to that described in Example 2E(1), first paragraph, but rather than evaporating the organic solvent, wash the reaction mixture with water, dry the organic phase over anhydrous sodium sulfate, and evaporate to a residue.

Purify the resultant residue as usual by preparative thin-layer chromatography, using chloroform:ethyl acetate (19:1) to develop the plates and ethyl acetate to extract the product. Crystallize from methylene chloride:hexane to obtain the purified title compound.

D. 6α-Fluoro-9α,21-Dichloro-16α-Methyl-1, 4-Pregnadiene-11β,17α-Diol-3,20-Dione 17-(2'-Furoate)

Dissolve the compound prepared in Example 10C(3) (0.974 gms.) in tetrahydrofuran (25 mls.) and cool to 15° C. Add perchloric acid (0.3 ml. of 70% perchloric acid in 0.7 ml. water), 1,3-dichloro-5,5-dimethylhydantoin (0.237 gms.), and stir under a nitrogen atmosphere at room temperature for 2 hours. Add the reaction mixture to a solution of sodium bisulfite in water (2 gms. in 250 ml.) and collect the solids to obtain the title compound.

Purify the crude product by chromatography on silica gel G-60, combine the desired components as determined by thin-layer chromatography and evaporate to give the purified product.

EXAMPLE 11

9 α,11β-DICHLORO-16α-METHYL-1, 4-PREGNADIENE-17α, 21-DIOL-3,20-DIONE 17-(2'-THENOATE)

A. 9α,11β-Dichloro-16α-Methyl-1, 4-Pregnadiene-17α, 21-Diol-3,20-Dione 17α,21-Orthothenoate Dissolve 9α,11β-dichloro-16α-methyl-1, 4-pregnadiene-17α,21-diol-3, 20-dione (2 gms.) in a mixture of dioxane (20 ml.) and benzene (60 ml.) and reflux using a Dean-Stark take-off collector. After distilling off 20 ml. solvent, add 2-trimethylorthothenoate dissolved in benzene (182 gms. in 10 ml.) and pyridinium p-toluenesulfonate (0.072 gms.). Reflux for ten minutes with distillation and concurrent replacement of benzene. Repeat the addition of orthoester and pyridinium tosylate and the distillation step four more times.

Cool the reaction mixture to room temperature, add 3 drops of pyridine and evaporate in vacuo to a residue comprising the title compound.

B. 9α,11β-Dichloro-16α-Methyl-1, 4-Pregnadiene-17α,21-Dioi-3, 20-Dione 17-(2'-Thenoate)

Dissolve the residue prepared in Example 11A in acetic acid (35 ml. of a 90% solution in water) and stir at room temperature for 24 hours. Add the reaction mixture to water (300 ml.) and extract with ethyl acetate to obtain the title compound. Purify the crude material by crystallization from methylene chloride:hexane and by preparative thin-layer chromatography as usual, using chloroform:ethyl acetate (9:1) as developing solvent.

EXAMPLE 12

9α,21-DICHLORO-11β, 17α-DIHYDROXY-16α-METHYL-1, 4-PREGNADIENE-3,20-DIONE 17-(2'-FUROATE)

METHOD I

A. 21-Chloro-9β, 11β-epoxy-17α-hydroxy-16α-methyl-1, 4-pregnadiene-3,20-dione

Prepare a solution of 5.0 g. of 9β,11βepoxy-17α, 21-dihydroxy-16α-methyl-1, 4-pregnadiene-3,20-dione in 20 ml. of dry pyridine. Cool on an ice bath; to the stirred solution under nitrogen, add dropwise 1.1 ml of mesyl chloride. Remove the ice bath and continue stirring at room temperature for 30 minutes. Add 2.0 gm. of lithium chloride and continue stirring for a further 150 minutes. Add to a mixture of 150 ml ethyl acetate and 100 ml distilled water in a separatory funnel. Wash the organic phase with dilute 3% aqueous hydrochloric acid, then saturated aqueous sodium chloride solution and finally saturated aqueous sodium bicarbonate solution. Dry the organic phase over magnesium sulfate, filter and remove the solvent. Recrystallise the methylene chloride:diethyl ester to give from the combined crops 4.62 gm. of the title compound.

B. 21-Chloro-9β, 11β-epoxy-17α-hydroxy-16α-methyl-1, 4-pregnadiene-3,20-dione 17-(2'-furoate)

Prepare under argon a solution of 8 gm. of 4-dimethylamino-pyridine in 250 ml of dry methylene chloride. Cool on an ice bath and add to the stirred solution 6.0 ml of 2-furoyl chloride. Remove from the ice bath, allow the temperature to rise to room temperature and then add 11.5 gm. of the product of Step A. After 24 hours add under rapid stirring 500 ml. of ethyl acetate saturated with water. Filter off the precipitate and then evaporate off the solvent from the filtrate to give the crude title product which was used without further purification in Step C.

C. 9α,21-Dichloro-11β, 17α-dihydroxy-16α-methyl-1, 4-pregnadiene-3,20-dione 17-(2'-furoate)

To the product of Step B add 50 ml. of glacial acetic acid. To the stirred solution under argon, then add a solution of 3.5 gm. of anhydrous hydrogen chloride in 125 ml. of glacial acetic acid. Stir for 15 minutes and then quench with 500 ml of distilled water. Filter off the solids, recrystallise from methanol:water, dry for 24 hours under vacuum to give 12.6 gm. of the title compound (yield 83% of theory).

METHOD II

Prepare under nitrogen a solution of 1.80 gms. of 21-chloro-17α-hydroxy-16α-methyl-1, 4,9(11)-pregnatriene-3,20-dione 17-(2'-furoate) [obtained in a manner similar to that described in Example 10C(3)] in 39 ml of dry tetrahydrofuran.

Maintain under nitrogen and cool on an ice bath. Add, with stirring, a solution of 1.15 ml of 70% perchloric acid in 2.53 ml of distilled water, and immediately thereafter 604 mg. of 1,3 dichloro-5,5-dimethylhydantoin. Stir the reaction mixture for twenty minutes and then raise the temperature to ambient temperature. Monitor the consumption of starting material by thin layer chromatography of aliquots using chloroform:ethyl acetate (9:1) and hexane:ethyl acetate (1:1). When the starting material is consumed, pour the reaction mixture into 500 ml. of distilled water containing 7 gms. of sodium bisulphite. Add sodium chloride until the solution is saturated. Filter the precipitated solid, wash copiously and dry at 50° C. under vacuum.

Purify the resulting crude product by preparative chromatography on 1000 micron silica gel plates using chloroform: ethyl acetate (19:1). Elute the desired band with ethyl acetate, filter the eluate and evaporate at room temperature to give crude product (1.3 gm). Recrystallize the product by dissolving in refluxing methylene chloride, filtering and then replacing the methylene chloride at reflux with methanol and then the methanol with distilled water. Cool the suspension to room temperature, filter and dry under vacuum at 50° C. to give the pure title product: λmax 247 mn (ε24,940); mass spectrum (no parent ion) 486, 484, 374, 372, 331, 313, 295, 277, 121, 95.

EXAMPLE 13

9α-CHLORO-21-FLUORO-11β, 17β-DIHYDROXY-16α-METHYL-1, 4-PREGNADIENE-3,20-DIONE 17-(2'-FUROATE)

A. 21-Fluoro-17α-hydroxy-16α-methyl-1, 4,9(11)-pregnatriene-3,20-dione 17-(2'-furoate)

Stir at room temperature a mixture of 1.411 gm. of 21-fluoro-17α-hydroxy-16α-methyl-1, 4,9(11)-pregnatriene-3,20-dione (made by the procedure of Herz et al., JACS, 78, 4812 (1956)), 1.623 gm. of furioc anhydride and 1.923 gm of 4-dimethylamino-pyridine in 16 ml of methylene chloride for 5 days until thin layer chromatography indicates 80–85% reaction. Air-evaporate the methylene chloride, triturate the residue with water and then collect the solid product by filtration. Dry the product at 50° C. under vacuum (yield 1.79 g.). Purify the crude product by preparative thin layer chromatography on 1000 micron silica gel plates using a chloroform:ethyl acetate mixture (first 9:1 and then 19:1 ratio) as developing solvent. Elute the desired band with ethyl acetate, filter the eluate and evaporate at room temperature to give a residue of 1.35 gm. (yield 75.8% of theory). Recrystallise the product twice from methylene chloride to yield white needles of 21-fluoro-17α-hydroxy-16α-methyl-1, 4,9(11)pregnatriene-3, 20-dione 17-(2'-furoate) (764 mg.; yield 43% of theory): λmax 246.5 nm (ε25,430); mass spectrum: 452, 437, 340, 325, 307, 279, 224, 171, 95.

B. 9α-Chloro-21-fluoro-11β, 17α-dihydroxy-16α-methyl-1, 4-pregnadiene-3,20-dione 17-(2'-furoate)

To a cooled solution (0°–2° C.) maintained under nitrogen of 538.5 mg. of the product obtained by Step A in 12 ml. of tetrahydrofuran, add with stirring a solution of 0.36 ml. of 70% perchloric acid in 0.8 ml. of distilled water and immediately thereafter 187.5 mg. of 1,3-dichloro-5,5-dimethylhydantoin. After 5 minutes remove the reaction mixture from the ice bath, discontinue the nitrogen flow and stir the reaction at room temperature for 150 minutes until consumption of the starting material is substantially complete as indicated by thin layer chromatography of aliquiots using hexane:ethyl acetate (2:1). Pour the product mixture into 700 ml of distilled water containing 2 gm. of sodium bisulphite. Add sodium chloride until the solution is saturated.

Filter off the precipitate, wash copiously with water and then dry at 60° C. under vacuum to give 597 mg. of crude product (yield 96% of theory).

Purify the crude product by preparative thin layer chromatography on 1000 micron silica gel plates using chloroform:ethyl acetate (9:1). Elute the desired band with ethyl acetate, filter the eluate, evaporate off the solvent and then triturate the residue with ether, discarding the supernatant liquor. Dry the product at room temperature (yield 440 mg). Recrystallise from a methylene chloride:hexane mixture at reflux temperature to give 375 mg. of the pure title compound: λmax 246 nm (methanol) (ε25,730); mass spectrum: 505, 504, 469, 468, 356, 331, 313, 295, 277, 121, 95.

EXAMPLE 14

9α-FLUORO-16α-METHYL-11β, 17α,21-TRIOL-1,4-PREGNADIENE-3,20-DIONE 17-(2'-FUROATE) 21-ACETATE

A. 9α-Fluoro-16α-methyl-11β, 17α,21-triol-1,4-pregnadiene-3,20-dione 11β-trifluoroacetate 21-acetate Prepare a solution of 1.36 gm. of trifluoroacetic anhydride in 10 ml. of pyridine. Add 5 ml. of this reagent, chilled to 0°-2° C., to a chilled solution of 434.5 mg. of dexamethasone acetate in pyridine. Stir for 15 minutes and then pour the resulting solution into 200 ml. of 3.6 N. sulfuric acid solution.

Filter off the green solid, wash with water, resuspend it in water, stir, filter again, wash and then dry under vacuum at room temperature. Purify the crude product by preparative chromatography on 1000 micron silica gel plates using chloroform: ethyl acetate (9:1). Extract the desired area with ethyl acetate, filter the extract and evaporate at room temperature. Solidify the crude product with diethyl ether and hexane and dry at 50° C. under vacuum to give the title compound (198 mg; yield 37% of theo:y).

B. 9α-Fluoro-16α-methyl-11β, 17α,21-trihydroxy-1,4-pregnadiene-3,20-dione 11β-trifluoroacetate 17-(2'-furoate) 21-acetate In a manner similar to that described in Example 2A treat, in methylene chloride, 150 mg. of the product of Step A with a reaction mixture of 2-furoyl chloride and 4-dimethylamino-pyridine, stirring the reaction mixture for 66 hours. Dilute the reaction mixture with methylene chloride, wash with water, then 1N HCl followed by dilute sodium carbonate solution and then water adjusted to pH 5–6. Dry the methylene chloride solution over magnesium sulfate, filter and then air evaporate to give a residue of 162 mg. Purify by chromatography on 1000 micron silica gel plates using chloroform:ethyl acetate as eluant as described in Example 2A. Dissolve the product in diethyl ether, filter, and then evaporate. Dry at 50° C. under vacuum to give 50 mg. of product.

C. 9α-Fluoro-16α-methyl-11β, 17α,21-trihydroxy-1,4-pregnadiene-3, 20-dione 17-(2'-furoate) 21-acetate Stir 21 mg of the product of Step B with 72 mg. of sodium benzoate in 2 ml. of methanol for 3 hours. Pour the reaction mixture into saturated aqueous sodium chloride solution Filter off the white precipitate, wash with water and then dry at room temperature.

Purify by treating with diethyl ether:hexane to give 25 mg. of the title product which is identical to the product obtained in Example 3B(1) by reduction of a corresponding 11-ketone.

I claim:

1. A 3,20-dioxo-1,4-pregnadiene of the following formula:

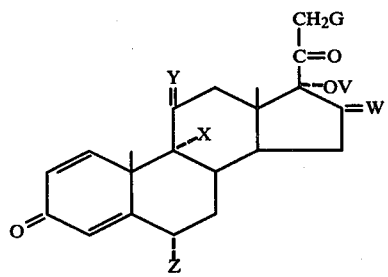

X is a member selected from the group consisting of hydrogen and halogen having an atomic weight less than 100;

Y is a member selected from the group consisting of (H,H) provided X is hydrogen, oxygen, (H,βOH), and (H,β-halogen) provided X is chlorine or bromine, said β-halogen having an atomic weight of less than 100 and being at least as electronegative as X;

Z is hydrogen, $CH_3$, chlorine, or fluorine;

V is an acyl radical of an aromatic heterocyclic carboxylic acid selected from the group consisting of thiophenecarboxylic acid, pyrrolecarboxylic acid and furancarboxylic acid, and methyl and halogen-substituted derivatives thereof;

W is a member selected from the group consisting of (H,H); (H, lower alkyl); (H, $OV_1$) wherein $V_1$ is a member selected from the group consisting of hydrogen and an acyl radical of an acid selected from the group consisting of a hydrocarboncarboxylic acid having up to 12 carbon atoms, benzoic acid substituted by a halogen or methoxy group, retinoic acid, and isonicotinic acid; =CHT wherein T is a member selected from the group consisting of hydrogen, lower alkyl, fluorine, and chlorine;

G is hydrogen, a halogen having an atomic weight less than 100, or $OV_2$ wherein $V_2$ is a member selected from the group consisting of hydrogen, an acyl radical of a hydrocarboncarboxylic acid having up to 12 carbon atoms, benzoic acid substituted by a halogen or methoxy group, retinoic acid, isonicotinic acid, and the acid radical of phosphoric acid and mono- and dialkali and alkaline earth metal salts thereof;

and the 6-dehydro and 1,2-dihydro analogs of the foregoing.

2. A 3,20-dioxo-1,4-pregnadiene of claim 1.

3. A compound of claim 2 wherein V is furan carbonyl.

4. A compound of claim 2 wherein V is thiophene carbonyl.

5. A compound of claims 3 or 4 wherein Z is fluorine.

6. A compound of claims 3 or 4 wherein G is chlorine.

7. A compound of claims 3 or 4 wherein G is lower alkanoyloxy.

8. A compound of claim 5 wherein W is α-methyl.

9. A compound of claim 6 wherein W is α-methyl.

10. A compound of claim 7 wherein W is α-methyl.

11. A compound of claim 1 having the following formula:

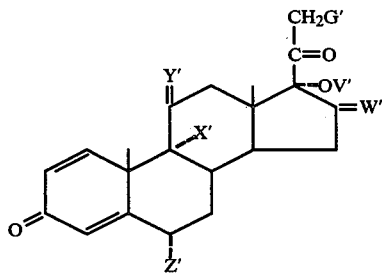

wherein W' is (H,H) or (H,CH₃); X' is fluorine or chlorine; Y' is (H,βOH) or (H,β-halogen) provided X' is chlorine, said β-halogen having an atomic weight of less than 100 and being at least as electronegative as X'; Z' is hydrogen or fluorine; V' is furan carbonyl or thiophene carbonyl; and G' is chlorine or OV₂', wherein V₂' is a member of the group consisting of hydrogen or an acyl radical of a hydrocarboncarboxylic acid having up to 12 carbon atoms, benzoic acid substituted by a halogen or methoxy group, retinoic acid, isonicotinic acid, and the acid radical of phosphoric acid and mono- and dialkali and alkaline earth metal salts thereof.

12. A compound according to claim 11 wherein V' is furan carbonyl.

13. A compound according to claim 11 wherein V' is thiophene carbonyl.

14. A compound according to claim 12 or 13 wherein W' is (H,α-methyl).

15. A compound of claim 14 wherein G' is chlorine.

16. A compound according to claim 15 wherein X' and Y' are each chlorine.

17. A compound according to claim 15 wherein X' is fluorine and Y' is (H,βOH).

18. A compound according to claim 15 wherein X' is chlorine and Y' is (H,βOH)

19. A compound according to claim 14 wherein G' is lower alkanoyloxy.

20. A compound according to claim 19 wherein X' and Y' are each chlorine.

21. A compound according to claim 19 wherein X' is fluorine and Y' is (H,βOH).

22. A compound according to claim 18 wherein V' is 2-furan carbonyl, said compound being 9α,21-dichloro-16α-methyl-1, 4-pregnadiene-11β,17α-diol-3, 20-dione 17-(2'-furoate).

23. A compound according to claim 16 wherein V' is 2-furan carbonyl, said compound being 9α,11β,21-trichloro-16α-methyl-1, 4-pregnadiene-17α-ol-3,20-dione 17-(2'-furoate).

24. A compound according to claim 21 wherein V' is 2-furan carbonyl and V₂' is acetyl, said compound being 9α-fluoro-16α-methyl-1, 4-pregnadiene-11β,17α,21-triol-3,20-dione 17-2'-furoate) 21-acetate.

25. A compound according to claim 16 wherein V' is 2-thiophene carbonyl, said compound being 9α,11β,21-trichloro-16α-methyl-1, 4-pregnadiene-17α-ol-3,20-dione 17-(2'-thenoate).

26. A compound according to claim 18 wherein V' is 2-thiophene carbonyl, said compound being 9α,21-dichloro-16α-methyl-1, 4-pregnadiene-11β,17α-diol-3, 20-dione 17-(2'-theonate).

27. A compound according to claim 21 wherein V' is 2-thiophene carbonyl and V₂' is acetyl, said compound being 9α-fluoro-16α-methyl-1, 4-pregnadiene-11β,17α,21-triol-3, 20-dione 17-(2'-thenoate) 21-acetate.

28. A pharmaceutical composition for use in the treatment of inflammation which comprises an anti-inflammatorily effective amount of a 3,20-dioxo-1,4-pregnadiene-17α-ol 17-aromatic heterocyclic carboxylate of claim 1 together with a non-toxic, pharmaceutically acceptable carrier.

29. A pharmaceutical composition of claim 28 for use in the treatment of inflammation which comprises a topical, anti-inflammatorily effective amount of the compound of claim 11.

30. The method of treating an inflammatory condition in a warm-blooded animal responsive to treatment with anti-inflammatory agents which comprises administering to said animal a non-toxic, anti-inflammatorily effective amount of a 3,20-dioxo-1,4-pregnadiene-17α-ol 17-aromatic heterocyclic carboxylate of claim 1 together with a non-toxic, pharmaceutically acceptable carrier.

31. The method according to claim 30 for the treatment of a topical inflammatory condition which comprises applying to the inflamed area in a concentration effective for the topical treatment of inflammation a 3,20-dioxo-1,4-pregnadiene-17α-ol 17-aromatic heterocyclic carboxylate of claim 11, together with a non-toxic, pharmaceutically acceptable carrier.

* * * * *